(12) United States Patent
Huang et al.

(10) Patent No.: US 6,312,459 B1
(45) Date of Patent: Nov. 6, 2001

(54) STENT DESIGN FOR USE IN SMALL VESSELS

(75) Inventors: Howard H. Huang; Timothy A. Limon, both of Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/343,849

(22) Filed: Jun. 30, 1999

(51) Int. Cl.[7] .................................................. A61F 2/06
(52) U.S. Cl. ............................................... 623/1.15
(58) Field of Search ........................... 623/1.15–1.16, 623/1.3–1.31, 1.18–1.19

(56) References Cited

U.S. PATENT DOCUMENTS

| | | | |
|---|---|---|---|
| 5,514,154 | * | 5/1996 | Lau et al. ............................... 623/1 |
| 5,735,893 | * | 4/1998 | Lau et al. ............................... 623/1 |
| 5,928,280 | * | 7/1999 | Hansen et al. ......................... 623/1 |
| 5,938,697 | * | 8/1999 | Killion et al. .......................... 623/1 |

OTHER PUBLICATIONS

Charnsangavej, Chuslip, M.D., et al., Stenosis of the Vena Cava: Preliminary Assessment of Treatment with Expandable Metallic Stents, *Radiology*, pp. 295–298, vol. 161, Nov. 1986.
Rösch, Josef, M.D., et al., Experimental Intrahepatic Portacaval Anastomosis: Use of Expandable Gianturco Stents, *Radiology*, pp. 481–485, vol. 162, No. 1987.
Rösch, Josef, M.D., et al., Modified Gianturco Expandable Wire Stents In Experimental and Clinical Use, *Annales de Radiologie*, pp. 100–103, vol. 31, No. 2, 1998.
Lawrence, David D., Jr., et al., Percutaneous Endovascular Graft: Experimental Evaluation, *Radiology*, pp. 357–360, vol. 163, May 1987.
Rösch, Josef, et al., Gianturco Expandable Stents In Experimental and Clinical Use, pp. 121–124. Twelfth Annual Course on "Diagnostic Angiography and Interventional Radiology" Mar. 23–26, 1987, San Diego, California.

\* cited by examiner

*Primary Examiner*—Cary E. O'Connor
(74) *Attorney, Agent, or Firm*—Fulwider Patton Lee Utecht, LLP

(57) ABSTRACT

An expandable stent design for use in small vessels, such as the distal regions of the coronary arteries, is disclosed. The stent consists of a plurality of radially expandable cylindrical elements generally aligned on a common longitudinal stent axis and interconnected by one or more interconnecting members placed so that the stent is flexible in a longitudinal direction. The strut width of the interconnecting members is narrower than the strut width of each cylindrical element thereby increasing the flexibility of the interconnecting members relative to the struts of the cylindrical elements. In one particular embodiment of the present invention, the strut width of the connecting segment between alternating peaks and valleys of the cylindrical element is designed to be wider than the width of the strut in the peak and valley portions of the cylindrical element to enhance the radiopacity of the stent. The stent pattern of the present invention is particularly well suited for use in small vessels having diameters of less than three millimeters, such as the distal vessels of the coronary arteries.

17 Claims, 3 Drawing Sheets

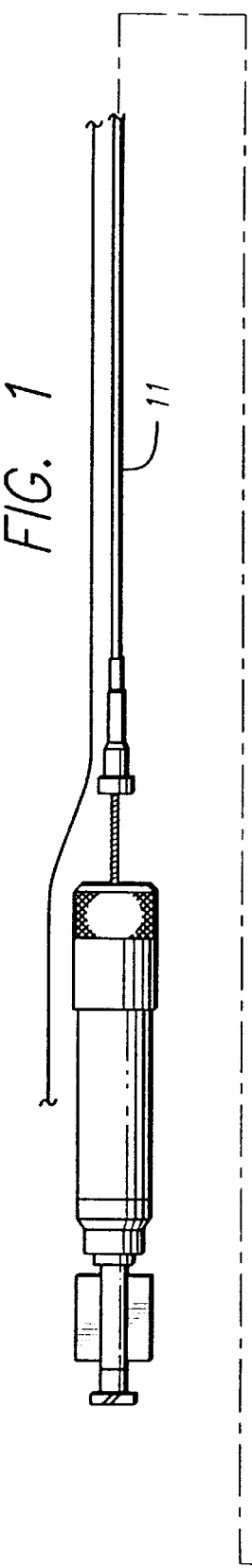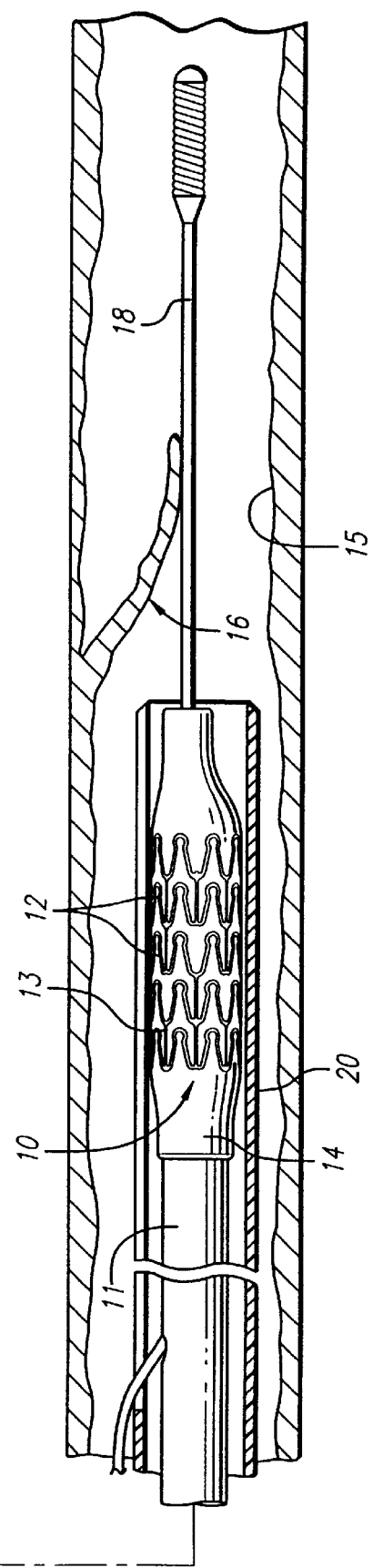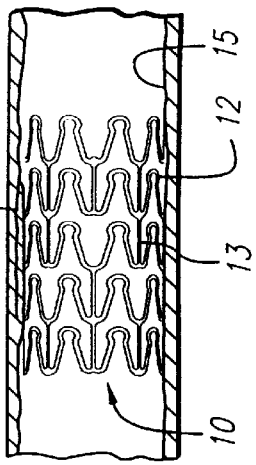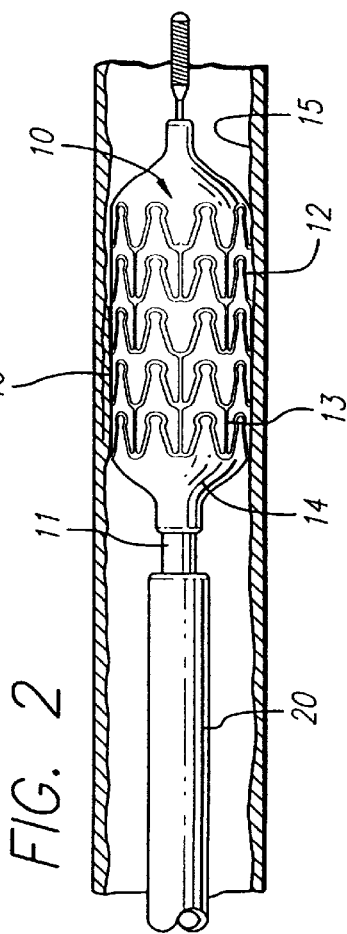

STENT DESIGN FOR USE IN SMALL VESSELS

BACKGROUND OF THE INVENTION

The present invention relates to expandable endoprosthesis devices, generally called stents, which are adapted to be implanted into a patient's body lumen, such as a blood vessel, to maintain the patency thereof. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis.

Stents are generally cylindrically shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from shape memory metals or super-elastic nickel-titanum (NiTi) alloys, which will automatically expand from a compressed state when the stent is advanced out of the distal end of the delivery catheter into the blood vessel. Such stents manufactured from expandable heat sensitive materials allow for phase transformations of the material to occur, resulting in the expansion and contraction of the stent.

Details of prior art expandable stents can be found in U.S. Pat. No. 3,868,956 (Alfidi et al.); U.S. Pat. No. 4,512,1338 (Balko et al.); U.S. Pat. No. 4,553,545 (Maas, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallstent); U.S. Pat. No. 4,739,762 (Palmaz); and U.S. Pat. No. 5,569,295 (Lam), which are hereby incorporated by reference.

Further details of prior art self-expanding stents can be found in U.S.

Pat. No. 4,580,568 (Gianturco); and U.S. Pat. No. 4,830,003 (Wolff, et al.), which are hereby incorporated by reference.

Expandable stents are delivered to the target site by delivery systems which often use balloon catheters s the means for delivering and expanding the stent in the target area. One such stent delivery system is disclosed in U.S. Pat. No. 5,158,548 to Lau et al. Such a stent delivery system has an expandable stent in a contracted condition placed on an expandable member, such as an inflatable balloon, disposed on the distal portion of an elongated catheter body. A guide wire extends through an inner lumen within the elongated catheter body and out its distal end. A tubular protective sheath is secured by its distal end to the portion of the guide wire which extends out of the distal end of the catheter body and fits over the stent mounted on the expandable member on the distal end of the catheter body.

Some prior art stent delivery systems for implanting self-expanding stents include an inner lumen upon which the compressed or collapsed stent is mounted and an outer restraining sheath which is initially placed over the compressed stent prior to deployment. When the stent is to be deployed in the body vessel, the outer sheath is moved in relation to the inner lumen to "uncover" the compressed stent, allowing the stent to move to its expanded condition into the target area.

In many procedures which utilize stents to maintain the patency of the patient's body lumen, the size of the body lumen can be quite small which prevents the use of some commercial stents which have profiles which are entirely too large to reach the small vessel. In particular, often in PTCA procedures, the stenosis is located in the very distal regions of the coronary arteries which often have diameters less than three millimeters. Many of these distal lesions are located deep within the tortuous vasculature of the patient which requires the stent to not only have a small profile, but also high flexibility to be advanced into these regions. As a result, the stent must be sufficiently flexible along its longitudinal axis, yet be configured to expand radially to provide sufficient strength and stability to maintain the patency of the body lumen. Since many commercial stents lack both the low profile and extreme flexibility needed to reach such distal lesions, they are not available for utilization for such procedures.

What has been needed is a small vessel stent which has a low profile and a high degree of flexibility so that it can be advanced through tortuous passage ways of the anatomy and can be expanded within small vessels to maintain the patency of the vessel. Additionally, the expanded stent must have adequate structural strength (hoop strength) to hold the body lumen open once expanded. Such a stent should also have sufficient radiopaque properties to permit it to be sufficiently visualized on external monitoring equipment, such as a fluoroscope, to allow the physician to place the stent in the exact target location. The present invention satisfies these needs.

SUMMARY OF INVENTION

The present invention is directed to stents having extremely low profiles which can be used in small vessels, such as the distal vessels of the coronary arteries. The stents of the present invention are intended, but are not limited, to the effective treatment of diseased vessels having diameters less than 3.0 millimeters. In one preferred embodiment of the present invention, the stent design can be used in a diseased vessel at least as small as 1.0 millimeter.

In all embodiments, the small vessel stents of the present invention have sufficient longitudinal flexibility along their longitudinal axis to facilitate delivery through tortuous body lumens, yet remain stable when expanded radially to maintain the patency of a body lumen such as an artery or other vessel, when implanted therein. The present invention in particular relates to unique patterns which permit greater longitudinal flexibility and sufficient radial-expansibility and strength to hold open small diameter body lumens.

Each of the different embodiments of stents of the present invention include a plurality of adjacent cylindrical elements (often referred to as "rings") which are generally expandable in the radial direction and arranged in alignment along a longitudinal stent axis. The cylindrical elements are formed in a variety of serpentine wave patterns transverse to the longitudinal axis and contain a plurality of alternating peaks and valleys. At least one interconnecting member extends between adjacent cylindrical elements and connects them to one another. These interconnecting members insure a minimal longitudinal contraction during radial expansion of the stent in the body vessel. The serpentine patterns have varying degrees of curvature in the regions of peaks and valleys and are adapted so that radial expansion of the cylindrical elements are generally uniform around their circumferences during expansion of the stent from the contracted condition to the expanded condition.

In one preferred embodiment of the present invention, each cylindrical element of the stent includes five peak regions (often referred to as "crowns") and five valley regions which help reduce the overall profile of the stent in its unexpanded or contracted condition (sometimes referred to as the "crimp profile"). The crimp profile of the stent can be further reduced by decreasing the width of the strut of the interconnecting members connecting adjacent cylindrical elements and reducing the amount of metal in the tips of the peaks (or crowns). This decrease of the width of the strut of the interconnecting members also helps increase the flexibility of these interconnecting struts relative to the struts of the cylindrical elements. The resulting stent produces a five crown, three-cell pattern which has sufficient coverage for vessel scaffolding and maintains excellent flexibility to reach distal lesions, while still possessing sufficient radial strength to hold the target vessel open. The decrease in width of the interconnecting members must not be so great as to compromise sufficient column strength in maintaining the spacing between the rings.

In another preferred embodiment of the present invention, the strut width of the segments connecting the alternating peaks and valley regions can be increased to enhance the overall radiopacity of the stent. In this fashion, the strut width in those areas or regions of the stent which have little or no effect on the flexibility of the stent can be increased to enhance the overall radiopacity of the stent. Alternatively, these same regions of the stent can be designed with thicker struts which adds mass to the stent which also increases the radiopacity of the stent. The stent can also be coated or plated with radiopaque material to increase the overall radiopacity of the stent, as may be needed. The coating of the stent can also help to increase the biocompatibility of the stent.

Preferably, the number and location of the interconnecting members can be varied in order to develop the desired longitudinal flexibility in the stent structure both in the unexpanded as well as the expanded state. The use of fewer interconnecting members usually results in a more flexible design since this "frees up" more of the highly flexible U-shaped peaks. Thus, flexibility is derived mainly from the rings while the number and location of the interconnecting members influences the flexibility by constraining or "freeing up" the U-shaped members. Generally, the greater the longitudinal flexibility of the stents, the easier and the more safely they can be delivered to the implantation site, especially where the implantation site is on a curved section of a body lumen, such as a coronary artery or peripheral blood vessel, and especially in saphenous veins and larger vessels. However, if increased vessel scaffolding is desired, the number of interconnecting members can be increased as needed.

The resulting stent structures are a series of radially expandable cylindrical elements that are spaced longitunally close enough so that small dissections in the wall of a body lumen may be pressed back into position against the lumenal wall, but not so close as to compromise the longitudinal flexibility of the stent both when negotiating through the body lumens in their unexpanded state and when expanded into position. Each of the individual cylindrical elements may rotate slightly relative to their adjacent cylindrical elements without significant deformation, cumulatively providing stents which are flexible along their length and about their longitudinal axis, but which still are very stable in their radial direction in order to resist collapse after expansion.

The stents of the present invention can be readily delivered to the desired target location by mounting it on an expandable member, such as a balloon, of a delivery catheter and passing the catheter-stent assembly lumen to the target area. A variety of means for securing a stent to the extendible member of the catheter for delivery to the desired location are available. It is presently preferred to crimp or compress the stent onto the unexpanded balloon. Other means to secure the stent to the balloon included providing ridges or collars on the inflatable member to restrain lateral movement, using bioabsorbable temporary adhesives, or adding a retractable sheath to cover the stent during delivery through a body lumen. When a stent of the present invention is made from a self-expanding material such as nickel titanium alloy, a suitable stent delivery assembly which includes a retractable sheath, or other means to hold the stent in its expanded condition prior to deployment, can be utilized.

The serpentine pattern of the individual cylindrical elements can optionally be in phase with each other in order to reduce the contraction of the stent along their length when expanded. The cylindrical elements of the stent are plastically deformed when expanded (except with Niti alloys) so that the stent will remain the expanded condition and therefore must be sufficiently rigid when expanded when expanded to prevent the collapsed thereof during use.

When the stents are formed from super elastic nickel titanium alloys, the expansion occurs when the stress of compression is removed. This allows the phase transformation from martensite back to austenitite to occur, and as a result the stent expands.

These and other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, depicting the stent embodying features of the present invention mounted on a delivery catheter disposed within a vessel.

FIG. 2 is an elevational view, partially in section, similar to that shown in FIG. 1, wherein the stent is expanded within a vessel, pressing the lining against the vessel wall.

FIG. 3 is an elevational view, partially in section, showing the expanded stent within the vessel after withdrawal of the delivery catheter.

DETAILED DESCRIPTION OF THE PREFERRED EMBODIMENTS

Prior art stent designs, such as the MultiLink Stent™ manufactured by Advanced Cardiovascular Systems, Inc., Santa Clara, Calif., include a plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical element or ring. A more detailed discussion of the configuration of the MultiLink Stent™ can be found in U.S. Pat. No. 5,569,295 (Lam) and U.S. Pat. No. 5,514,154 (Lau et al.), whose contents are hereby incorporated by reference.

Figure 5:
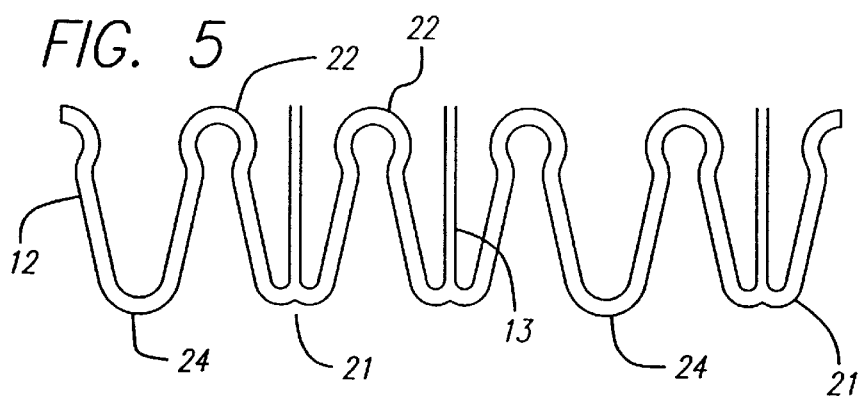
FIG. 5 is an enlarged partial view of the stent of FIG. 4 depicting the serpentine pattern along with the peaks and valleys which form one preferred embodiment of a cylindrical element made in accordance with the present invention.

Beyond those prior art stents, FIG. 1 illustrates an exemplary embodiment of stent 10 incorporating features of the present invention, which stent is mounted onto delivery catheter 11. FIG. 5 is a plan view of this exemplary embodiment stent 10 with the structure flattened out into two dimensions to facilitate explanation. Stent 10 generally comprises a plurality of radially expandable cylindrical elements 12 disposed generally coaxially and interconnected by interconnecting members 13 disposed between adjacent cylindrical elements 12. The delivery catheter 11 has an expandable portion or balloon 14 for expanding stent 10 within artery 15 or other vessel. The artery 15, as shown in FIG. 1, has a dissected or detached lining 16 which has occluded a portion of the arterial passageway.

The delivery catheter 11 onto which stent 10 is mounted is essentially the same as a conventional balloon dilatation catheter for angioplasty procedures. The balloon 14 may be formed of suitable materials such as polyethylene, polyethylene terephthalate, polyvinyl chloride, nylon and, ionomers such as Surlyn® manufactured by the Polymer Products Division of the Du Pont Company. Other polymers may also be used.

In order for stent 10 to remain in place on balloon 14 during delivery to the site of the damage within artery 15, stent 10 is compressed or crimped onto balloon 14. A retractable protective delivery sleeve 20 may be provided to ensure that stent 10 stays in place on balloon 14 of delivery catheter 11 and to prevent abrasion of the body lumen by the open surface of stent 10 during delivery to the desired arterial location. Other means for securing stent 10 onto balloon 14 also may be used, such as providing collars or ridges on the ends of the working portion, i.e., the cylindrical portion, of balloon 14. Each radially expandable cylindrical element 12 of stent 10 may be substantially independently expanded. Therefore, balloon 14 may be provided with an inflated shape other than cylindrical, e.g., tapered, to facilitate implantation of stent 10 in a variety of body lumen shapes. When the stent 10 is made from a self-expanding material such as Nitinol, a suitable delivery device with retractable sleeve may be used to deploy the stent.

In a preferred embodiment, the delivery of stent 10 is accomplished in the following manner. Stent 10 is first mounted onto inflatable balloon 14 on the distal extremity of delivery catheter 11. Stent 10 may be crimped down onto balloon 14 to obtain a low profile. The catheter-stent assembly can be introduced within the patient's vasculature in a conventional Seldinger technique through a guiding catheter (not shown). Guidewire 18 is disposed through the damaged arterial section with the detached or dissected lining 16. The catheter-stent assembly is then advanced over guide wire 18 within artery 15 until stent 10 is directly under detached lining 16. Balloon 14 of catheter 11 is inflated or expanded, thus expanding stent 10 against the inside of artery 15, which is illustrated in FIG. 2. While not shown in the drawing, artery 15 is preferably expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid there through.

While FIGS. 1–3 depict a vessel having detached lining 16, stent 10 can be used for purposes other than repairing the lining. Those other purposes include, for example, supporting the vessel, reducing the likelihood of restenosis, or assisting in the attachment of a vascular graft (not shown) when repairing an aortic abdominal aneurysm.

In general, stent 10 serves to hold open artery 15 after catheter 11 is withdrawn, as illustrated in FIG. 3. Due to the formation of stent 10, the undulating component of the cylindrical elements of stent 10 is relatively flat in a transverse cross-section so that when stent 10 is expanded, cylindrical elements 12 are pressed into the wall of artery 15 and as a result do not interfere with the blood flow through artery 15. Cylindrical elements 12 of stent 10 that are pressed into the wall of artery 15 will eventually be covered with endothelial cell growth that further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 15, and consequently are well adapted to tack up and hold in place small flaps or dissections in the wall of artery 15 as illustrated in FIGS. 2 and 3.

Figure 4:
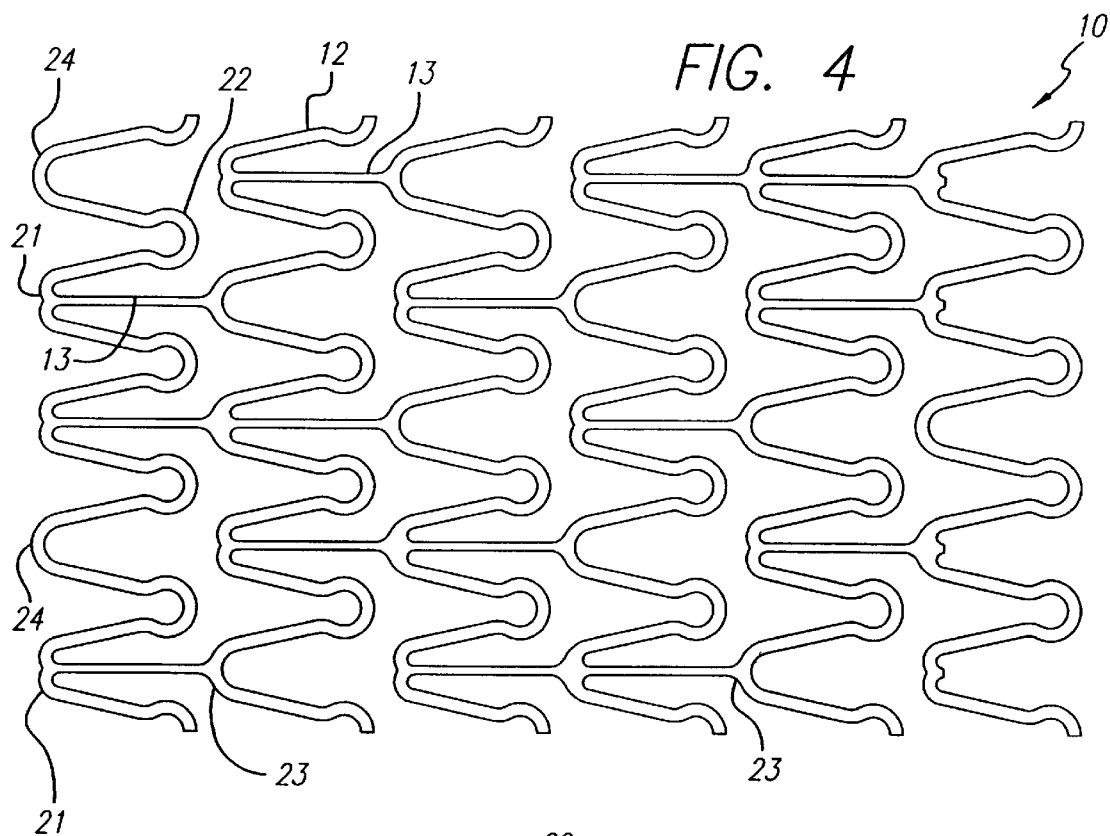
FIG. 4 is a plan view of one preferred embodiment of a flattened stent of the present invention, which illustrates the serpentine pattern including peaks and valleys which form the cylindrical elements of the stent and permit the stent to achieve a small crimp profile, yet is expandable to a larger diameter to maintain the patency of a small vessel.
Figure 6:
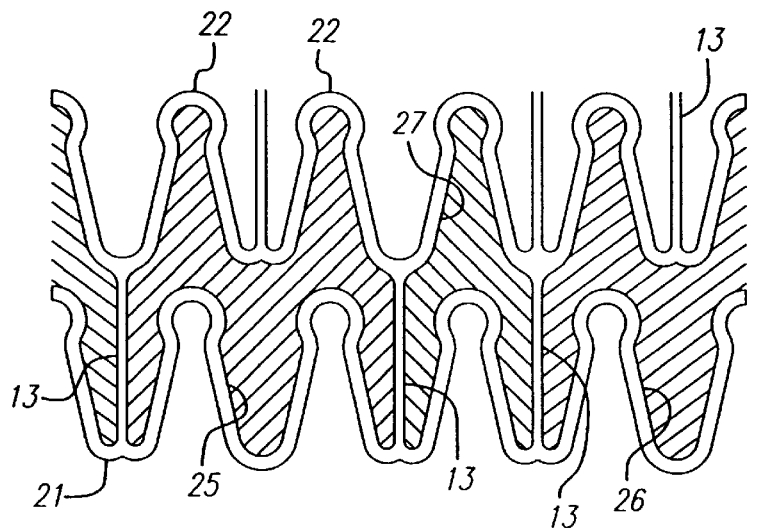
FIG. 6 is an enlarged partial view of the stent of FIG. 4 depicting two cylindrical elements which form the cell patterns of a stent made in accordance with the present invention.

The stresses involved during expansion from a low profile to an expanded profile are generally evenly distributed among the various peaks and valleys of stent 10. Referring to FIGS. 4–6, one preferred embodiment of the present invention as depicted in FIGS. 1–3 is shown wherein each expanded cylindrical element 12 embodies a serpentine pattern having a plurality of peaks and valleys that aid in the even distribution of expansion forces. In this exemplary embodiment, interconnecting members 13 serve to connect adjacent valleys of each adjacent cylindrical element 12 as described above. The various peaks and valleys generally have U, Y, W and inverted-U shapes, in a repeating pattern to form each cylindrical element 12. It should be appreciated that the cylindrical element 12 can be formed in different shapes without departing from the spirit and scope of the present invention.

The cylindrical element 12 of this stent 10 includes the double-curved portion (W) 21 located in the region of the valley where each interconnecting member 13 is connected to an adjacent cylindrical element 12. The peak portion (inverted-U) 22, the valley portion (Y) 23 and valley portion (U) 24 also form a cylindrical element 12 of the stent 10. During radial expansion, these regions are susceptible to high stresses and strains which can cause cracks to form in the stent if the width of the strut is too large. If the strut widths are increased in the areas designated by the double-curved portion (W) 21, peak portion (inverted-U) 22, valley portion (Y) 23 and valley portion (U) 24, the strain in the material would increase dramatically and could cause cracks to occur or may prevent the stent from fully deploying into its enlarged diameter during radial expansion, which is highly undesirable when deploying the stent 10 into the target region.

As can be seen in FIGS. 4–6, the interconnecting member 13 has a strut width which is narrower than the strut width found on the cylindrical element 12. While the presence of interconnecting members 13 actually decreases the flexibility of the stent as compared to, for example, cylindrical elements 12 arranged on a balloon but not interconnected, the reduction of the width or thickness of the existing interconnecting members 13 allows them to become flexible, as compared to similar thicker interconnected members. The reduced strut width of the interconnecting members 13 results a more flexible strut design as compared to the thicker struts of the connecting members, which helps when deploying the stent into tortuous distal vessels. Although this particular stent pattern includes three interconnecting members connecting adjacent cylindrical elements 12 together, it is possible to use more or less interconnecting members. Generally, less interconnecting members result in a more flexible stent since the primary flexibility in the stent results from the cylindrical elements and especially the unsupported and unconstrained U-shaped elements. Of course, it is still possible to add interconnecting members if needed, to increase vessel scaffolding.

Referring now to FIG. 6, a portion of the stent consisting of two adjacent cylindrical elements 12 with three interconnecting members connecting each element 13 together is shown. The enclosed area (identified by the hatching) between adjacent cylindrical elements 12 and interconnecting members 13 form what is commonly referred to as a "cell." In the particular embodiment of the stent shown in FIGS. 4–6, a three-cell pattern is disclosed. Two of the cells 25 and 26 of this three-cell pattern include two peak regions ("crowns") while the smaller third cell 27 only has a single peak region ("crown"). The use of this smaller third cell 27 decreases the crimp profile of stent allowing the stent to be utilized in body vessels which can be three millimeters or less. This smaller third cell 27 does not compromise the structural integrity of the stent or the ability of the stent to successful scaffold the walls of the target vessel, once implanted.

Figure 7:
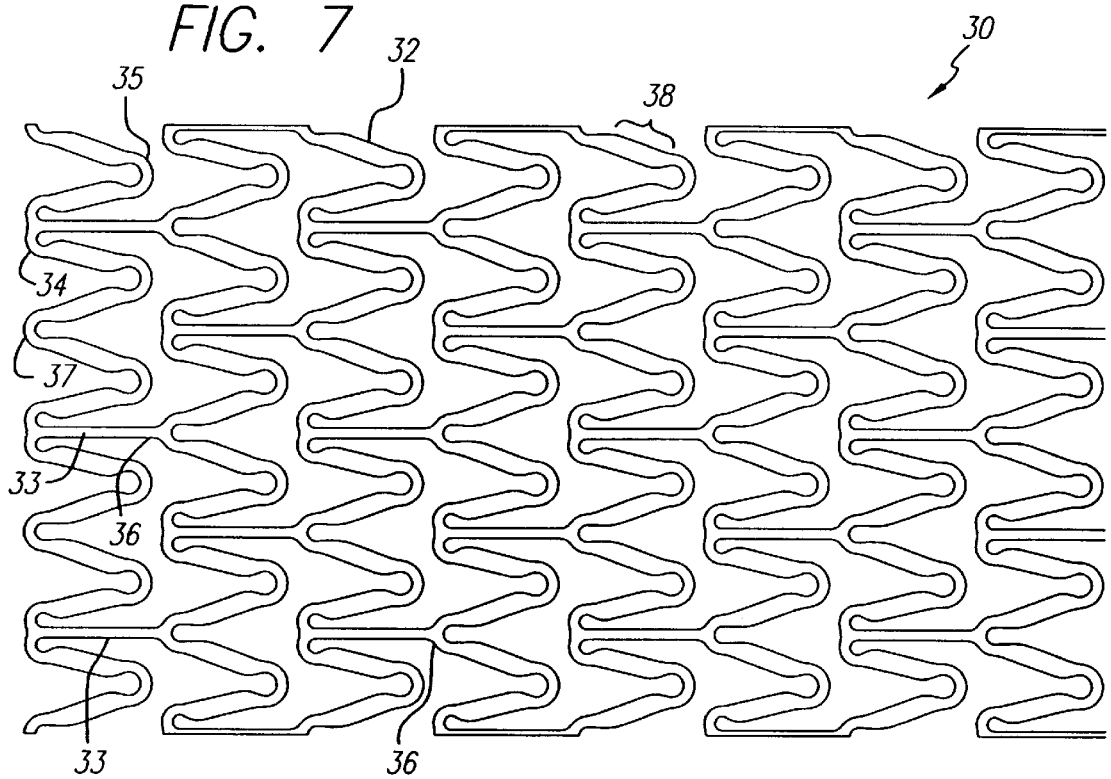
FIG. 7 is a plan view of an alternative preferred embodiment of a flattened stent of the present invention, which illustrates the serpentine pattern along with the peaks and valleys which form the cylindrical elements of the stent and permit the stent to achieve a small crimp profile, yet is expandable to a larger diameter to maintain the patency of a small vessel.
Figure 8:
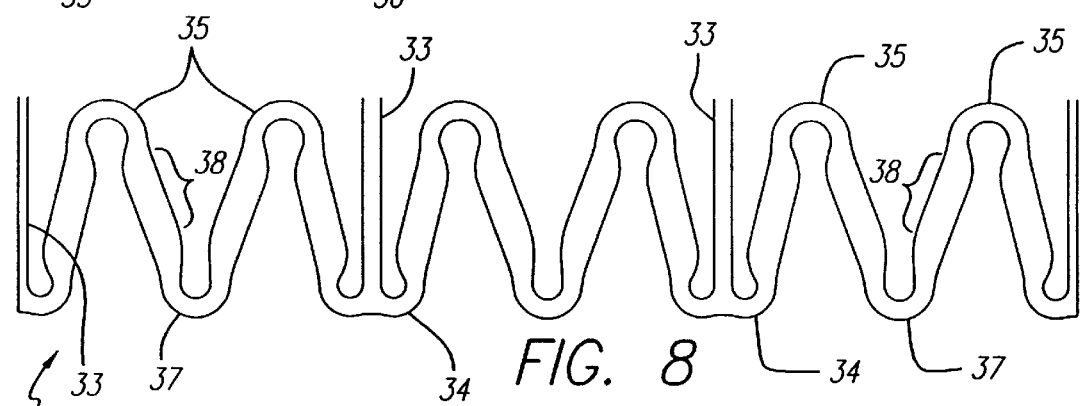
FIG. 8 is an enlarged partial view of the stent of FIG. 7 depicting the serpentine pattern along with the peaks and valleys which form another preferred embodiment of a cylindrical element made in accordance with the present invention.
Figure 9:
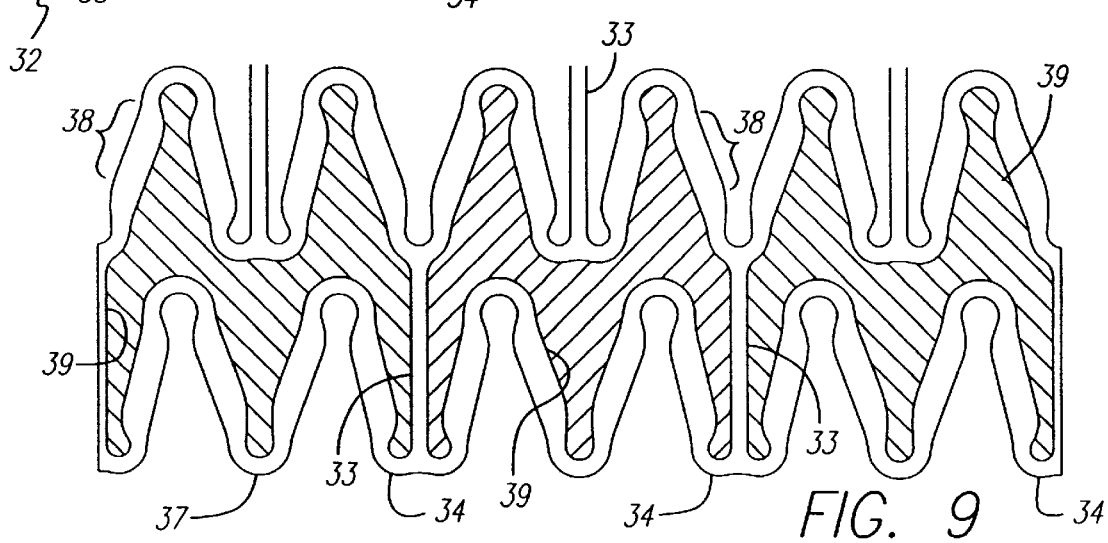
FIG. 9 is an enlarged partial view of the stent of FIG. 7 depicting two cylindrical elements which form the cell regions of a stent made in accordance with the present invention.

Referring now to FIGS. 7–9, another preferred embodiment of the present invention using the concept of increasing the strut width in low stress regions of the stent is shown. In this particular embodiment, the stent 30 includes cylindrical elements 32 which includes peaks and valleys having U, Y, W and inverted-U shapes, in repeating patterns to form each individual cylindrical element. Each cylindrical element 32 is connected to an adjacent cylindrical element via an interconnecting member 33. The high stress region of this stent 30 include the double-curved portion (W) 34, located in the region of valley where each interconnecting member 33 is connected to an adjacent cylindrical element 32. The peak portion (inverted-U) 35, the valley portion (Y) 36 and valley portion (U) 37 are also high stress regions of the stent. During radial expansion, these high stress regions are susceptible to high stresses and strains which can cause cracks to form in the stent if the width of the strut is too large. In the design of a stent of the present invention, the strut width is set in these high stress regions to meet the material strain, radial strength and expansile requirements of the stent. If the strut widths are increased in the areas designated by the double-curved portion (W) 34, peak portion (inverted-U) 35, valley portion (Y) 36 and valley portion (U) 37, the strain in the material would increase dramatically and could cause cracks to occur or may prevent the stent from fully deploying to its larger diameter during radial expansion, which again is a highly undesirable occurrence when deploying the stent into a target region.

The stent 10 also has low stress regions which include connecting segments 38 which extend from the peak portion (inverted-U) 35 to a valley portion of the cylindrical element 32. The increased strut width of connecting segment 38 enhances the overall radiopacity of the stent 30, with little or no effect on the mechanical properties or the profile of the stent. By increasing the strut width or thickness in regions of the stent which have little or no impact on the flexibility or mechanical properties (i.e., strength) of the stent, the radiopacity of the stent can be enhanced.

Referring specifically now to FIG. 9, two adjacent cylindrical elements 32 connected by three interconnecting members 33 are shown. Again, the hatching in FIG. 9 shows the enclosed area which forms the cells 39 of this particular stent 30. Again, a three-cell pattern is used in this particular embodiment. Each cell 39 has two peaks or crowns 35 resulting in a six crown, three-cell pattern. While this particular embodiment of the stent utilizes an additional crown, it still can be designed to have a very low crimp profile allowing the stent to be placed in vessels having diameters of less than 3 millimeters.

The interconnecting members 33 of the stent 30 also have narrower strut widths than the struts making up the various cylindrical elements 32 of the stent 30. The reduced strut width for these interconnecting members 33 again increases the flexibility of these struts as compared to the other stent struts and also helps to reduce the overall crimp profile of the device as well.

In many of the drawing figures, the present invention stent is depicted flat, in a plan view for ease of illustration. All of the embodiments depicted herein are cylindrically-shaped stents that are generally formed from tubing by laser cutting as described below.

One important feature of all of the embodiments of the present invention is the capability of the stents to expand from a low-profile diameter to a larger diameter, while still maintaining structural integrity in the expanded state and remaining highly flexible. Stents of the present invention each have an overall expansion ratio of about 1.0 up to about 4.0 times the original diameter, or more, using certain compositions of stainless steel. For example, a 316L stainless steel stent of the invention can be radially expanded from a diameter of 1.0 unit up to a diameter of about 4.0 units, which deforms the structural members beyond the elastic limit. The stents still retain structural integrity in the expanded state and will serve to hold open the vessel in which they are implanted. Materials other than stainless steel (316L) may afford higher or lower expansion ratios without sacrificing structural integrity.

While the present invention utilizes an increase of the width of connecting segments 38 to increase the overall radiopacity of the stent, the interconnecting segments 33 could have an increase of width which adds mass to the stent to increase the radiopacity as well. Alternatively, the stent could be coated or plated with additional radiopaque material to enhance the overall radiopacity of the stent.

It should be appreciated that the stent disclosed in FIGS. 4–6 could also be designed with connecting segments which are wider than the peak and valley portions of the cylindrical element to enhance the overall radiopacity of the stent.

Generally, the flexibility of the stent can also be increased by decreasing the number of interconnecting members which are utilized to connect the adjacent cylindrical elements. Additionally, if increased vessel scaffolding is desired, the number of interconnecting members could be increased, as needed.

While the stent design of the present invention has very practical applications for procedures involving vessel diameters of less than three millimeters, it should be appreciated that the stent pattern could also be successfully used in procedures involving larger lumens of the body, without departure from the spirit and scope of the present invention. Due to the increase of the longitudinal flexibility provided by the present stent design, such applications could include larger diameter vessels where added flexibility in reaching the vessel is needed.

The stents of the present invention can be made in many ways. However, the preferred method of making the stent is to cut a thin-walled tubular member, such as stainless steel tubing to remove portions of the tubing in the desired pattern for the stent, leaving relatively untouched the portions of the metallic tubing which are to form the stent. It is preferred to cut the tubing in the desired pattern by means of a machine-controlled laser.

The tubing may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | .025% max. |
| Sulphur (S) | 0.010% max. |
| Silicon (Si) | 0.75% max. |
| Chromium(Cr) | .17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameters are very small, so the tubing from which it is made must necessarily also have a small diameter. For PTCA applications, typically the stent has an outer diameter on the order of about 1 mm (0.04–0.09 inches) in the unexpanded condition, the same outer diameter of the hypotubing from which it is made, and can be expanded to an outer diameter of 4.0 mm or more. The wall thickness of the tubing is about 0.076 mm (0.003–0.006 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. No. 5,759,192 (Saunders) and U.S. Pat. No. 5,780,807 (Saunders), which have been assigned to Advanced Cardiovascular Systems, Inc. and are incorporated herein by reference in their entirely.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of Nitinol used in the manufacture of a self expanding stent of the present invention is approximately 55% nickel and 45% titanium (by weight) with trace amounts of other elements making up about 0.5% of the composition. The austenite transformation temperature is between about −150° C. and 0° C. in order to achieve superelastecity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of Nitinol can be utilized, as can other self-expanding alloys, to obtain the same features of a self-expanding stent made in accordance with the present invention.

The stent of the present invention can be laser cut from a tube of super-elastic (sometimes called pseudo-elastic) nickel titanium (Nitinol) whose transformation temperature is below body temperature. All of the stent diameters are cut with the same stent pattern, and the stent is expanded and heat treated to be stable at the desired final diameter. The heat treatment also controls the transformation temperature of the Nitinol such that the stent is super elastic at body temperature. The transformation temperature is at or below body temperature so that the stent is superelastic at body temperature. The stent is electro polished to obtain a smooth finish with a thin layer of titanium oxide placed on the surface. The stent is usually implanted into the target vessel which is smaller than the stent diameter so that the stent applies a force to the vessel wall to keep it open.

The stent tubing of a self expanding stent made in accordance with the present invention may be made of suitable biocompatible material besides super-elastic nickel-titanium (NiTi) alloys. In this case the stent would be formed full size but deformed (e.g. compressed) to a smaller diameter onto the balloon of the delivery catheter to facilitate intra luminal delivery to a desired intra luminal site. The stress induced by the deformation transforms the stent from an austenite phase to a martensite phase, and upon release of the force when the stent reaches the desired intra luminal location, allows the stent to expand due to the transformation back to the more stable austenite phase. Further details of how NiTi super-elastic alloys operate can be found in U.S. Pat. No. 4,665,906 (Jervis) and U.S. Pat. No. 5,067,957 (Jervis).

While the invention has been illustrated and described herein in terms of its use as intra vascular stents, it will be apparent to those skilled in the art that the stents can be used in other instances in all conduits in the body, such as, but not limited to, the urethra and esophagus. Other modifications and improvements may be made without departing from the scope of the invention.

What is claimed is:

1. A longitudinally flexible stent for implanting in a body lumen and expandable from a contracted condition to an expanded condition, comprising:

a plurality of adjacent cylindrical elements, each cylindrical element having a circumference extending about a longitudinal stent axis and being substantially independently expandable in the radial direction, wherein the plurality of adjacent cylindrical elements are arranged in alignment along the longitudinal stent axis and form a generally serpentine wave pattern transverse to the longitudinal axis containing alternating valley portions and peak portions with connecting segments interconnecting said valley portions and peak portions;

a plurality of interconnecting members extending between the adjacent cylindrical elements to connect adjacent cylindrical elements to one another, said interconnecting members have strut widths narrower than the strut widths of said cylindrical elements, and wherein at least one cylindrical element has connecting segments which have strut widths wider than the strut widths of the valley portions and peak portions of said cylindrical elements.

2. The stent of claim 1, wherein each of said cylindrical elements has connecting segments having strut widths which are wider than the strut widths of the valley portions and peak portions of said cylindrical elements.

3. The stent of claim 1, wherein the stent is formed from a biocompatible material selected from the group consisting of stainless steel, tungsten, tantalum, superelastic nickel titanium alloys, or thermal plastic polymers.

4. A stent for implanting in a body lumen, comprising:

a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent and containing alternating valley portions and peak portions; and a plurality of interconnecting members extending between cylindrical elements to connect adjacent cylindrical elements, each pair of adjacent cylindrical elements and the interconnecting members connecting those adjacent cylindrical elements forming a plurality of cells, each cell being defined by a pair of adjacent interconnecting members and the portion of the adjacent cylindrical elements connected between the pair of adjacent interconnecting members, wherein one of the cells formed between adjacent cylindrical elements has only one peak portion and the cells other than the single peak cell each have a plurality of peak portions.

5. The stent of claim 4, wherein each interconnecting member and cylindrical element has a strut width, the strut width of the interconnecting members being narrower than the strut width of the cylindrical elements.

6. The stent of claim 4, wherein three interconnecting members connect adjacent cylindrical elements to form three cells between each pair of adjacent cylindrical elements.

7. The stent of claim 4, wherein each interconnecting member and cylindrical element has a strut width, the strut width of the interconnecting members being narrower than the strut width of the cylindrical elements.

8. The stent of claim 4, wherein the stent is formed from a biocompatible material selected from the group consisting of stainless steel, tungsten, tantalum, superelastic nickel titanium alloys, and thermal plastic polymers.

9. A stent for implanting in a body lumen, comprising:

a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent and containing alternating valley portions and peak portions; and a plurality of interconnecting members extending between cylindrical elements to connect adjacent cylindrical elements, each pair of adjacent cylindrical elements and the interconnecting members connecting those adjacent cylindrical elements forming a plurality of cells, each cell being defined by a pair of adjacent interconnecting members and the portion of the adjacent cylindrical elements connected between the pair of adjacent interconnecting members, wherein one of the cells formed between adjacent cylindrical elements has only one peak portion and each cylindrical element includes five alternating peak portions and five valley portions with three interconnecting members connecting cylindrical elements together, each pair of adjacent cylindrical elements and interconnecting members forming three cells, wherein two of the cells each includes two peak portions.

10. A stent for implanting in a body lumen, comprising:

a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent and containing alternating valley portions and peak portions; and a plurality of interconnecting members extending between cylindrical elements to connect adjacent cylindrical elements, each pair of adjacent cylindrical elements and the interconnecting members connecting those adjacent cylindrical elements forming a plurality of cells, each cell being defined by a pair of adjacent interconnecting members and the portion of the adjacent cylindrical elements connected between the pair of adjacent interconnecting members, wherein one of the cells formed between adjacent cylindrical elements has only one peak portion and connecting segments connect each of the valley portions to the peak portions, at least one cylindrical element having connecting segments with strut widths that are wider than the strut widths of the valley portions and peak portions of the cylindrical element.

11. The stent of claim 10, wherein each of said cylindrical elements has connecting segments having strut widths that are wider than the strut widths of the valley portions and peak portion of the cylindrical element.

12. A stent for implanting in a body lumen, comprising:

a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent and containing alternating valley portions and peak portions; and a plurality of interconnecting members extending between adjacent cylindrical elements to connect adjacent cylindrical elements together, two of the interconnecting members being arranged adjacent to one another such that only one peak portion of a cylindrical element is connected between the adjacent interconnecting members and wherein the cells other than the single peak cell each have a plurality of peak portions.

13. The stent of claims 12, wherein each interconnecting member and cylindrical element has a strut width, the strut width of the interconnecting members being narrower than the strut width of the cylindrical elements.

14. The stent of claim 12, wherein three interconnecting members connect each adjacent cylindrical element.

15. The stent of claim 12, wherein the stent is formed from a biocompatible material selected from the group consisting of stainless steel, tungsten, tantalum, superelastic nickel titanium alloys, and thermal plastic polymers.

16. The stent of claim 12, wherein each interconnecting member and cylindrical element has a strut width, the strut width of the interconnecting members being narrower than the strut width of the cylindrical elements.

17. A stent for implanting in a body lumen, comprising:

a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent and containing alternating valley portions and peak portions; and a plurality of interconnecting members extending between adjacent cylindrical elements to connect adjacent cylindrical elements together, two of the interconnecting members being arranged adjacent to one another such that only one peak portion of a cylindrical element is connected between the adjacent interconnecting members and wherein each cylindrical element includes five alternating peak portions and five valley portions with three interconnecting members connecting cylindrical elements together.

* * * * *

UNITED STATES PATENT AND TRADEMARK OFFICE
CERTIFICATE OF CORRECTION

PATENT NO.   : 6,312,459 B1               Page 1 of 1
DATED        : November 6, 2001
INVENTOR(S)  : Howard R. Huang et al.

It is certified that error appears in the above-identified patent and that said Letters Patent is hereby corrected as shown below:

<u>Column 9,</u>
Table, line 58, change ".17.00-19.00%", to read -- 17.00-19.00% --.

Signed and Sealed this

Twenty-fifth Day of June, 2002

*Attest:*

*Attesting Officer*

JAMES E. ROGAN
*Director of the United States Patent and Trademark Office*